United States Patent
Balthasar et al.

(10) Patent No.: US 10,669,220 B2
(45) Date of Patent: Jun. 2, 2020

(54) METHOD FOR THE SYNTHESIS OF METHANOL

(71) Applicant: GASCONTEC AG, Basel (CH)

(72) Inventors: Wolff Balthasar, Ratingen (DE); Dierk Müller, Karben (DE); Ulrich Wagner, Bernburg (DE)

(73) Assignee: GASCONTEC GMBH, Bad Homburg V. D. Höhe (DE)

( * ) Notice: Subject to any disclaimer, the term of this patent is extended or adjusted under 35 U.S.C. 154(b) by 0 days.

(21) Appl. No.: 16/076,939

(22) PCT Filed: Feb. 10, 2017

(86) PCT No.: PCT/EP2017/053039
§ 371 (c)(1),
(2) Date: Aug. 9, 2018

(87) PCT Pub. No.: WO2017/137581
PCT Pub. Date: Aug. 17, 2017

(65) Prior Publication Data
US 2019/0047931 A1    Feb. 14, 2019

(30) Foreign Application Priority Data
Feb. 11, 2016    (EP) .................................... 16155353

(51) Int. Cl.
*C07C 29/151*    (2006.01)
*B01J 8/04*    (2006.01)
(Continued)

(52) U.S. Cl.
CPC ......... *C07C 29/1518* (2013.01); *B01J 8/0457* (2013.01); *B01J 8/0492* (2013.01);
(Continued)

(58) Field of Classification Search
CPC .. C01B 3/56; C01B 3/38; C01B 3/382; C01B 3/52; C01B 2203/127; C01B 2203/061;
(Continued)

(56) References Cited

U.S. PATENT DOCUMENTS 4,181,675 A    1/1980  Makin et al.
4,464,483 A *  8/1984  de Lathouder ..... C07C 29/1512
                                                    518/703
(Continued)

FOREIGN PATENT DOCUMENTS

CN    103232321 A1    8/2013
EP      2281793 A1    2/2011
(Continued)

OTHER PUBLICATIONS

International Search Report dated Jun. 12, 2017 re: Application No. PCT/EP2017/053039, pp. 1-2, citing: WO 36/21634 A1, WO 2006/126017 A1 and EP 2 281 793 A1.

*Primary Examiner* — Jafar F Parsa
(74) *Attorney, Agent, or Firm* — Cantor Colburn LLP

(57) ABSTRACT

A method for the synthesis of methanol includes the steps of feeding a hydrogen-containing stream from a hydrogen recovery stage into a synthesis gas stream containing hydrogen and carbon oxides, and feeding the synthesis gas stream to a primary reactor stage for the catalytic and partial conversion of the synthesis gas stream into a gas mixture containing water, methanol, and residual gas, and further including the step of feeding a first portion of the residual gas to the hydrogen recovery stage for separation into the hydrogen-containing stream and a waste gas stream. The method is characterized in that a second portion of the residual gas is fed to a secondary reactor stage for further catalytic and at least partial conversion into a methanol-containing product stream.

15 Claims, 4 Drawing Sheets

(51) Int. Cl.
   *C01B 3/52*   (2006.01)
   *C01B 3/38*   (2006.01)
   *C01B 3/56*   (2006.01)
   *C07C 31/04*  (2006.01)
   *B01J 23/80*  (2006.01)

(52) U.S. Cl.
   CPC ........... *B01J 8/0496* (2013.01); *C01B 3/38* (2013.01); *C01B 3/382* (2013.01); *C01B 3/52* (2013.01); *C01B 3/56* (2013.01); *C07C 29/1516* (2013.01); *C07C 31/04* (2013.01); *B01J 23/80* (2013.01); *B01J 2208/0053* (2013.01); *B01J 2208/00176* (2013.01); *C01B 2203/0244* (2013.01); *C01B 2203/042* (2013.01); *C01B 2203/0415* (2013.01); *C01B 2203/061* (2013.01); *C01B 2203/0827* (2013.01); *C01B 2203/127* (2013.01); *C01B 2203/1241* (2013.01); *Y02P 20/132* (2015.11)

(58) Field of Classification Search
   CPC ...... C01B 2203/042; C01B 2203/0244; C01B 2203/0415; C07C 31/04; C07C 29/1516; C07C 29/1518; Y02P 20/132; B01J 8/0492; B01J 8/0496; B01J 8/0457; B01J 2208/00176; B01J 2208/0053
   See application file for complete search history.

(56) References Cited

U.S. PATENT DOCUMENTS

| | | |
|---|---|---|
| 4,546,111 A | 10/1985 | Banquy |
| 4,782,096 A | 11/1988 | Banquy |
| 5,827,901 A | 10/1998 | Konig et al. |
| 2007/0225385 A1 | 9/2007 | Early |
| 2009/0018220 A1* | 1/2009 | Fitzpatrick .......... C07C 29/1518 518/700 |
| 2011/0178187 A1 | 7/2011 | Kopetsch |
| 2019/0016655 A1* | 1/2019 | Yiu ........................ C07C 31/04 |

FOREIGN PATENT DOCUMENTS

| | | |
|---|---|---|
| WO | 9621634 A1 | 7/1996 |
| WO | 2006061554 A1 | 6/2006 |
| WO | 2006126017 A1 | 11/2006 |
| WO | 2015193440 A1 | 12/2015 |

\* cited by examiner

METHOD FOR THE SYNTHESIS OF METHANOL

TECHNICAL FIELD

The disclosure relates to a method for the synthesis of methanol according to the preamble of Claim 1, and a system for the synthesis of methanol according to the preamble of Claim 15.

BACKGROUND

Methanol is generally produced in large facilities in which, in an intermediate step, fossil fuels such as coal or natural gas are initially converted into a synthesis gas composed of hydrogen and carbon oxides such as carbon monoxide in particular. A catalytic conversion of the synthesis gas into methanol subsequently takes place in an appropriate reactor. The methanol-containing product stream from the reactor is then cooled and fed to a separator to obtain crude methanol, with remaining residual gas being partially or completely circulated through the reactor.

Carbon monoxide and carbon dioxide with hydrogen may each be catalytically converted into methanol and possibly water in a manner known per se, wherein a molar ratio S, given by $$S = \frac{n(H_2) - n(CO_2)}{n(CO) + n(CO_2)},$$

of essentially 2.1, where n is expressed in moles, is sought for the most complete reaction possible of the carbon oxides and hydrogen. This molar ratio S is also referred to here and in the following discussion as the stoichiometry number. However, the synthesis gas frequently does not have such a molar ratio of essentially 2.1. In particular when synthesis gas is obtained by means of autothermal reformation, the stoichiometry number is between approximately 1.6 and 1.8, as the result of which the proportion of hydrogen is too low, and during the methanol synthesis a high proportion of carbon oxides remains. Since the remaining gas is generally circulated, the resulting increase in the gas volume to be recycled leads to drastic performance requirements for the compressors used, and requires a large quantity of catalyst for the methanol synthesis.

Various approaches are known from the prior art for approximating the desired value of the stoichiometry number by feeding hydrogen upstream from the methanol synthesis in terms of the process. For this purpose, WO 2006/126017 A1, from which the present disclosure proceeds, proposes to branch off a portion of the gas, as purge gas, remaining after the methanol synthesis, subsequent to the separation of crude methanol by condensation, and possibly to lead it through a pressure swing adsorption device (PSA). A portion of the synthesis gas is also fed prior to entry into the synthesis circuit of the PSA. The hydrogen thus obtained as well as the gas remaining after the methanol synthesis and not branched off are fed to the synthesis gas stream. The stoichiometry number may be set to the desired value by varying the proportion of the branched-off gas.

However, a disadvantage of this approach is that the carbon oxides in the gas fed to the PSA for the methanol synthesis are lost in a quantity that is proportional to the additional gain of hydrogen for the methanol synthesis. This reduces the yield of methanol relative to the source used for the generation of synthesis gas. Likewise, it is disadvantageous that, even under reaction conditions that are more favorable with regard to the stoichiometry, with the molar fractions of the carbon oxides to be applied here the methanol synthesis from the carbon monoxide preferentially takes place prior to the methanol synthesis from the carbon dioxide. As a result, the carbon dioxide from the synthesis gas is insufficiently used for the methanol synthesis, and is therefore circulated to a great extent without a synthesis reaction taking place, so that after circulation, large portions are discharged through the PSA. In addition, the increased volume flow in the circuit due in particular to the entrained carbon dioxide results in an increased requirement for catalyst volume.

SUMMARY

Based on conventional methods for producing methanol, the disclosure refines and improves the conventional method for methanol synthesis in such a way that a desired stoichiometry number is achievable, also with a reduced loss of carbon oxides, and in addition the efficiency with regard to the required compressor power and the quantity of catalyst is improved.

With regard to a method for the synthesis of methanol, this is achieved by providing a method wherein a hydrogen-containing stream from a hydrogen recovery stage is fed into a synthesis gas stream containing hydrogen and carbon oxides, and wherein the synthesis gas stream is fed to a primary reactor stage for the catalytic and partial conversion of the synthesis gas stream into a gas mixture containing water, methanol, and residual gas, and wherein a first portion of the residual gas is fed to the hydrogen recovery stage for separation into the hydrogen-containing stream and a waste gas stream, and wherein a second portion of the residual gas is fed to a secondary reactor stage for further catalytic and at least partial conversion into a methanol-containing product stream. With regard to a system for the synthesis of methanol, this is achieved by providing a feeding assembly for providing a synthesis gas stream with hydrogen and carbon oxides, comprising a hydrogen recovery stage from which a hydrogen-containing stream is fed into the synthesis gas stream, and comprising a primary reactor stage to which the synthesis gas stream is fed and in which the synthesis gas stream is catalytically and partially converted into a gas mixture with water, methanol, and residual gas, wherein a first portion of the residual gas is fed to the hydrogen recovery stage for separation into the hydrogen-containing stream and a waste gas stream, wherein the system has a secondary reactor stage to which a second portion of the residual gas is fed for further catalytic and at least partial conversion into a methanol-containing product stream.

Essential to the disclosure is the finding that the unreacted gas that remains after the methanol synthesis, and that is not fed to a hydrogen recovery stage such as a PSA in particular, may be fed to a secondary reactor stage for methanol synthesis, downstream from the primary reactor stage. In this way, the carbon dioxide, which is now present in the secondary reactor stage in a higher proportion with respect to the carbon monoxide in comparison to the ratios in the primary reactor stage, is for the most part converted into methanol. In addition to this direct utilization of the carbon dioxide, which otherwise would have been emitted as waste gas, there is also a reduction of the quantity of the circulated carbon dioxide, and thus, of the overall gas volume. This relieves load on the compressors that are necessary for the circulation, and allows a smaller volume of catalyst to be provided in the reactor stages.

The preferred embodiments in dependent claims 2 and 3 relate to particular molar ratios in the gas streams or in the reactor stages that are suitable overall for particularly complete methanol synthesis via both reactor stages.

The adjustability of the division of the gas streams for the hydrogen recovery stage on the one hand and for the secondary reactor stage on the other hand, provided by dependent claim 4, allows a dynamic response to changed reaction conditions or compositions of the synthesis gas stream.

Dependent claims 7 and 8, in turn, describe preferred embodiments for cooling the gas mixture from the primary reactor stage for the purpose of separating the crude methanol.

Dependent claim 9 describes particularly advantageous utilization of the synthesis gas stream for cooling the secondary reactor stage.

Dependent claim 10 relates to the advantageous provision of a further separation stage downstream from the secondary reactor stage and recycling the remaining unreacted gas as a secondary recycle stream, and dependent claim 11 relates to the advantageously increased molar fraction of carbon dioxide therein.

According to dependent claim 12, the proposed method is particularly suitable for synthesizing methanol from natural gas, in particular natural gas from a plurality of natural gas deposits, as an energy carrier, since it allows coordination with varying proportions of different hydrocarbons in the natural gas.

Dependent claim 13 relates to a particularly advantageous method for obtaining the synthesis gas from the carbon-containing energy carrier stream by autothermal reformation.

Lastly, dependent claim 14 describes a further embodiment via which the stoichiometry number for the methanol synthesis may be adjusted by an additional approach, even with varying compositions of the carbon-containing energy carrier stream and/or with a very high content of higher hydrocarbons.

BRIEF DESCRIPTION OF THE DRAWINGS

Further particulars, features, aims, and advantages of the present disclosure are explained below with reference to the drawings for one preferred exemplary embodiment, which show the following.

DETAILED DESCRIPTION OF THE DRAWINGS

Figure 1:
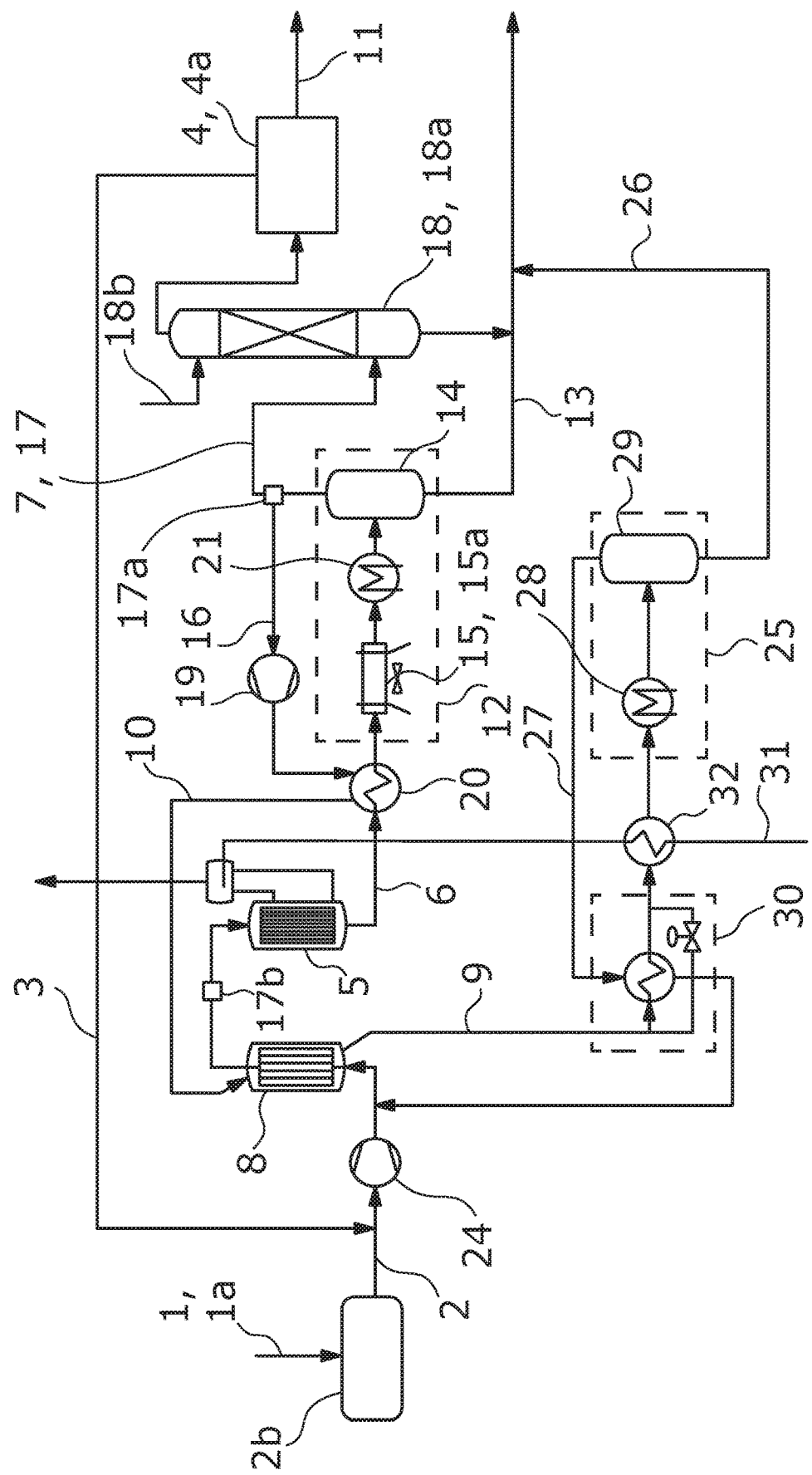
FIG. 1 shows the flow diagram of a system for carrying out the proposed method according to a first exemplary embodiment.

The proposed method is used for the synthesis of methanol, and is initially explained with reference to the exemplary embodiments in FIGS. 1 and 2. Unless stated otherwise, the following statements refer to both exemplary embodiments. In the proposed method, a hydrogen-containing stream 3 from a hydrogen recovery stage 4 is fed to a synthesis gas stream 2 containing hydrogen and carbon oxides, and the synthesis gas stream 2 is fed to a primary reactor stage 5. The synthesis gas stream 2 may in principle originate from any given source, although it is preferably obtained from a carbon-containing energy carrier stream 1, once again it being possible in principle for the synthesis gas stream 2 to be obtained in any given manner. Particulars concerning the energy carrier stream 1 and obtaining the synthesis gas stream 2 therefrom in the present exemplary embodiments are explained in greater detail below, in particular with reference to FIGS. 3 and 4. In the exemplary embodiment in FIG. 1, the obtained synthesis gas stream 2, prior to being fed with recycle streams or the like to be described below, has a volume flow rate of 601,473 $Nm^3/h$, and in the exemplary embodiment in FIG. 2 the obtained synthesis gas stream 2 has a volume flow rate of 602,188 $Nm^3/h$.

As proposed, feeding the synthesis gas stream 2 to the primary reactor stage 5 is used for the catalytic, partial conversion of the synthesis gas stream 2 into a gas mixture 6 containing water, methanol, and residual gas. This conversion is partial, in that unreacted synthesis gas remains as a component of the residual gas. This primary reactor stage 5 may also be made up of a plurality of individual reactors arranged in parallel or in series in terms of the process, which then as a whole form the primary reactor stage 5.

Figure 2:
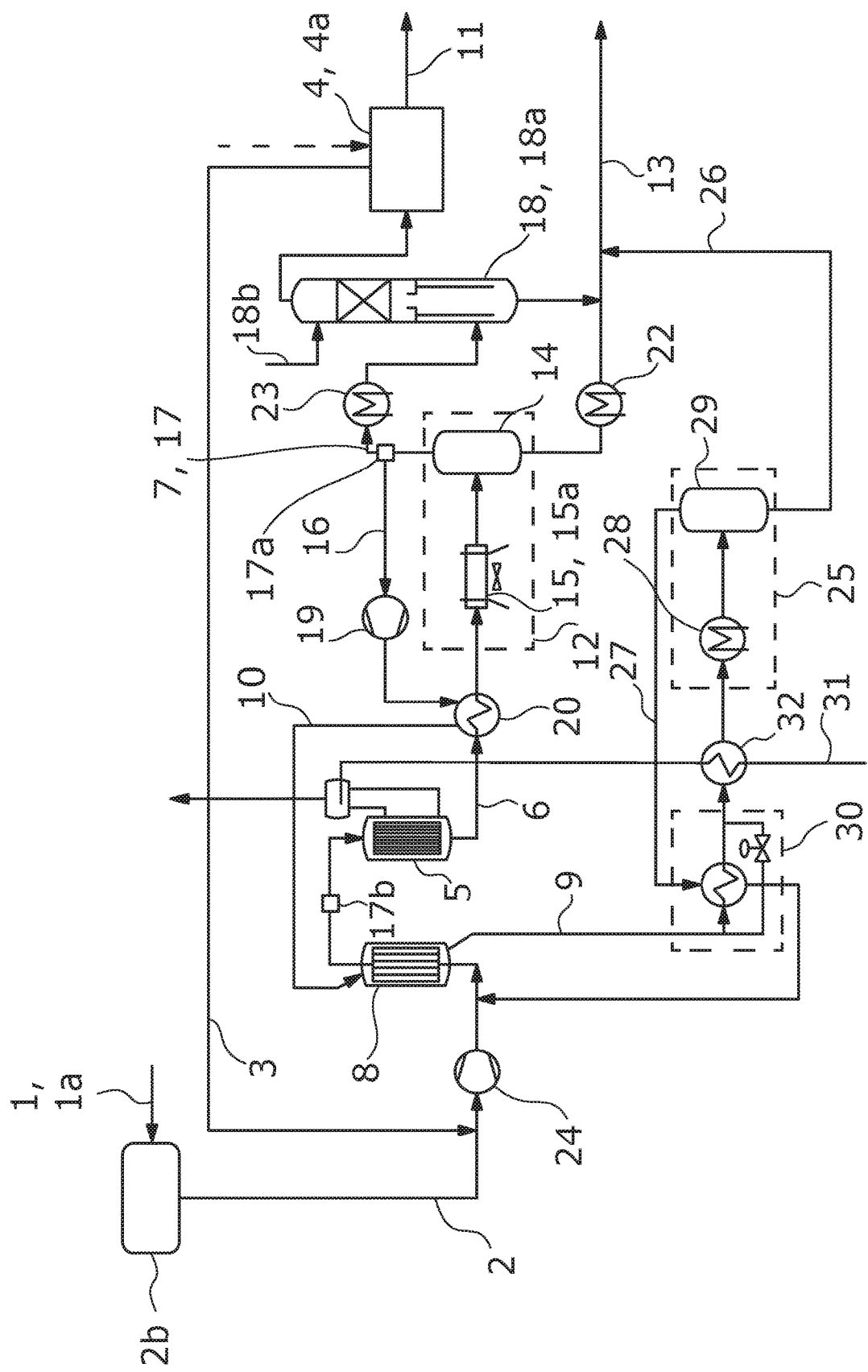
FIG. 2 shows the flow diagram of a system for carrying out the proposed method according to a second exemplary embodiment.

As an example of the exemplary embodiments in FIGS. 1 and 2, the synthesis gas stream 2 at a pressure of 74 bar and a temperature of 210° C. passes into the primary reactor stage 5. In the exemplary embodiment in FIG. 1, the fed synthesis gas stream 2 has a volume flow rate of 1,230,677 $Nm^3/h$, and in the exemplary embodiment in FIG. 2 has a volume flow rate of 1,201,410 $Nm^3/h$. The increase over the previously mentioned values results from the feeding to be described below. As a result of the exothermal synthesis reactions to produce methanol, known per se from the prior art, the gas mixture 6 exits from the primary reactor stage 5 at a temperature of 256° C. and a pressure of 72.7 bar. In the exemplary embodiment in FIG. 1, the gas mixture 6 has a volume flow rate of 1,014,516 $Nm^3/h$ and in the exemplary embodiment in FIG. 2 has a volume flow rate of 986,507 $Nm^3/h$. In addition to the hydrogen and the carbon oxides of the synthesis gas, the residual gas may contain further components, in particular inert gases in the present case. A copper-zinc oxide catalyst on an aluminum support, for example, may be used as catalyst for the methanol synthesis reactions, known per se, which take place in the primary reactor stage 5.

As proposed, a first portion 7 of the residual gas is fed to the hydrogen recovery stage 4 for separation into the hydrogen-containing stream 3 and a waste gas stream 11. In addition to the first portion 7 of the residual gas in the narrower sense, methanol and water may also be fed to the hydrogen recovery stage 4. The waste gas stream 11 may then be combusted or used in any other way. In the present case, the hydrogen recovery stage 4 is preferably a pressure swing adsorption device (PSA) 4a. In this case, the hydrogen-containing stream 3 is composed essentially of hydrogen, and the waste gas stream 11 contains the residual quantity of the first portion 7 of the residual gas remaining after separation of the hydrogen. In principle, however, some other approach may be used for hydrogen recovery by separation of the hydrogen-containing stream 3. As a result, the hydrogen-containing stream 3 may contain additional substances besides hydrogen. Thus, the hydrogen recovery stage 4 may have, or be, a scrubber device for selectively discharging carbon dioxide, so that the waste gas stream 11 is composed essentially of carbon dioxide. Accordingly, the hydrogen-containing stream 3 then contains inert gases in addition to hydrogen. In this variant, separate branching of purge gas may preferably be provided for the separation of inert gases, for which there are various options for placement of same in terms of the process. The hydrogen recovery stage 4 is fed with a volume flow rate of 240,182 Nm³/h in the exemplary embodiment in FIG. 1, and with a volume flow rate of 220,708 Nm³/h in the exemplary embodiment in FIG. 2. The hydrogen-containing stream 3 in the exemplary embodiment in FIG. 1 has a volume flow rate of 160,312 Nm³/h, and in the exemplary embodiment in FIG. 2 has a volume flow rate of 142,570 Nm³/h.

The proposed method is now characterized in that a second portion 10 of the residual gas is fed to a secondary reactor stage 8 for the further catalytic, at least partial, conversion into a methanol-containing product stream 9. Basically the same reactions for the synthesis of methanol proceed in the secondary reactor stage 8 as in the primary reactor stage 5; however, with regard to the type and design of the reactor, the catalyst used, and the criteria for the synthesis reaction, in particular the quantity and proportions of the starting materials, the pressure, and the temperature, the secondary reactor stage 8 and the synthesis reaction that proceeds therein may in principle be arbitrary, and generally different from the primary reactor stage 5 and the synthesis reaction in the primary reactor stage 5. A conversion of carbon dioxide to methanol of only approximately 30% to 40% takes place, while in the primary reactor stage 5 generally 80% of the carbon monoxide present is converted into methanol. The conversion of carbon dioxide into methanol once again predominates here due to the much higher molar fraction of carbon dioxide compared to carbon monoxide in the secondary reactor stage 8. This is described in greater detail below.

The same as discussed above for the primary reactor stage 5, the secondary reactor stage 8 may also be made up of a plurality of individual reactors arranged in parallel or in series in terms of the process. These individual reactors as a whole then form the secondary reactor stage 8. In the present case, gas enters the secondary reactor stage 8, which includes the second portion 10 of the residual gas, at a temperature of 210° C. and a pressure of 82.6 bar, by use of a compressor described in greater detail below. In addition to the second portion 10 of the residual gas 6 in the narrower sense, methanol and water may also enter the secondary reactor stage 8. The methanol-containing product stream 9 obtained from the methanol synthesis in the secondary reactor stage 8 enters at a temperature of 220° C. and a pressure of 77.8 bar, for example. In addition, a reaction that proceeds only partially may take place in the secondary reactor stage 8, so that the methanol-containing product stream 9 also generally contains methanol, water, and residual gas. Here as well, unreacted synthesis gas may be a remaining component of the residual gas.

One preferred embodiment is characterized in that the synthesis gas stream 2 prior to the hydrogen-containing stream 3 being fed has a molar ratio of S<2. This molar ratio S is given by $$S = \frac{n(H_2) - n(CO_2)}{n(CO) + n(CO_2)},$$

where n is expressed in moles. Thus, the synthesis gas stream 2 has a proportion of hydrogen that is too low for the methanol synthesis. This preferred embodiment is further characterized in that a molar ratio of S>2, preferably S>3, and in particular essentially S=4, is present in the primary reactor stage 5. The molar ratio in the primary reactor stage 5 is intended to mean the molar ratio S that results from the molar proportions of hydrogen, carbon monoxide, and carbon dioxide in the primary reactor stage 5 according to the stated formula. The above-mentioned feeding of the hydrogen-containing stream 3 thus even results in an excess of hydrogen in the primary reactor stage 5, which has advantageous effects on the reaction speed and the product quality, so that the generation of by-products is limited.

Another preferred embodiment is characterized in that in the secondary reactor stage 8 a molar ratio S, once again given by $$S = \frac{n(H_2) - n(CO_2)}{n(CO) + n(CO_2)},$$

where n is expressed in moles, is present which is greater than the molar ratio S present in the primary reactor stage 5. The molar ratio S is preferably greater by at least a factor of 1.5 or essentially by a factor of 1.5. Similarly as for the primary reactor stage 5, the molar ratio in the secondary reactor stage 8 is intended to mean the molar ratio S that results from the molar proportions of hydrogen, carbon monoxide, and carbon dioxide in the secondary reactor stage 8 according to the stated formula. The molar proportion of carbon monoxide in the sum of the molar quantities of hydrogen, carbon monoxide, and carbon dioxide in the secondary reactor stage 8 is less than the molar proportion of carbon monoxide in the sum of the molar quantities of hydrogen, carbon monoxide, and carbon dioxide in the primary reactor stage 5. In other words, in relation to the overall material quantity made up of the stated materials, the molar proportion of carbon monoxide in the secondary reactor stage 8 is less than the molar proportion of carbon monoxide in the primary reactor stage 5. As a result, the conversion of carbon dioxide into methanol increases in the secondary reactor stage 8, in particular due to the fact that sufficient carbon monoxide for this synthesis is no longer present.

A preferred embodiment is also provided according to which, and as illustrated in FIGS. 1 and 2, the first portion 7 of the residual gas and the second portion 10 of the residual gas are separated by means of a stream division of the gas mixture 6 into at least one primary recycle stream 16 for being fed to the secondary reactor stage 8, and a purge stream 17 for being fed to the hydrogen recovery stage 4. The primary recycle stream 16 includes the second portion 10 of the residual gas, and the purge stream 17 includes the first portion 7 of the residual gas. It is further preferred here that the volume ratio of the primary recycle stream 16 is adjustable to the purge stream 17. A corresponding valve assembly 17a for adjusting this volume ratio is schematically depicted in FIGS. 1 and 2. The option for adjusting the volume ratio of the primary recycle stream 16 to the purge stream 17, based on a composition of the synthesis gas stream 2, is particularly advantageous. This composition of the synthesis gas stream 2, in particular directly prior to feeding to the primary reactor stage 5, may be detected by a measuring assembly 17b, likewise schematically depicted here. A response may thus be made to dynamic changes, for example in the molar ratio of hydrogen in the synthesis gas stream 2, by increasing or decreasing the material quantity in the hydrogen-containing stream 3.

In order to obtain methanol remaining in the purge stream 17, the purge stream 17, as illustrated in the figures, prior to being fed to the hydrogen recovery stage 4 may be fed to a scrubbing stage 18 for scrubbing out methanol remaining in the purge stream 17. In this way, essentially the residual gas without methanol may be fed to the hydrogen recovery stage 4. In the present case, this scrubbing stage 18 is made up of a gas scrubber 18a. In the first exemplary embodiment in FIG. 1, a purge stream 17 having a volume flow rate of 240,998 Nm$^3$/h at 40° C. and a pressure of essentially 70 bar is fed to the gas scrubber 18a, in which scrubbing with 5000 kg/h water takes place at 40° C. This water is provided by a water feed 18b. In this way, crude methanol containing 1515 kg/h methanol is scrubbed out.

According to the exemplary embodiments, the primary recycle stream 16 together with the second portion 10 of the residual gas may then be fed to the secondary reactor stage 8, it being preferred that the primary recycle stream 16 is led through a recycle compressor 19 for the compression. In the exemplary embodiment in FIG. 1, the primary recycle stream 16 has a volume flow rate of 641,255 Nm$^3$/h, and in the exemplary embodiment in FIG. 2 has a volume flow rate of 645,472 Nm$^3$/h. In the present exemplary embodiments, the recycle compressor 19 thus increases the pressure of the primary recycle stream 16 of essentially 70 bar in this case to 83.1 bar. Likewise, for cooling the gas mixture 6 the primary recycle stream 16 may be led through a main recycle heat exchanger 20. As is apparent from the figures, for cooling the gas mixture 6 the gas mixture 6 is also led through the main recycle heat exchanger 20. This also results in heating of the primary recycle stream 16 to the above-mentioned temperature of 210° C.

As illustrated in the exemplary embodiments, the gas mixture 6 is preferably cooled and in particular fed to a separation stage 12 for separating a crude methanol stream 13. As illustrated in the exemplary embodiments, the gas mixture 6 is preferably essentially completely fed to the separation stage 12. The crude methanol stream 13 contains water and methanol, and in particular may be composed essentially of water and methanol. Generally only a portion of the methanol or water, not all of the methanol or all of the water, is separated from the gas mixture 6 via this separation stage 12. The separation stage 12 preferably has a deposition stage 14 which separates the crude methanol stream 13 as a condensate of the gas mixture 6. In the exemplary embodiments, the gas mixture 6 remaining after the deposition, i.e., the residual gas together with the uncondensed methanol and water, exits from the separation stage 12 and in particular from the deposition stage 14 at a pressure of essentially 70 bar. This methanol passes out of a sump of the gas scrubber 18a into the crude methanol stream 13 from the deposition stage 14, which in the exemplary embodiment in FIG. 1 contains 151,347 kg/h methanol in the crude methanol.

It may be further preferred here that the separation stage 12 has a cooling stage 15, which in particular may be an air cooling stage 15a, upstream from the deposition stage 14 for cooling the gas mixture 6. As an example, the second exemplary embodiment in FIG. 2 provides for cooling via this cooling stage 15 to a cooling temperature above the boiling point of methanol at standard pressure, and in particular, cooling to a temperature of 70° C.

It is further preferred that the above-mentioned cooling of the gas mixture 6 takes place prior to a division into the first portion 7 and the second portion 10 of the residual gas. The lower the temperature in the deposition stage 14, the more methanol that may be separated from the gas mixture 6. Therefore, in one preferred embodiment which is implemented in the first exemplary embodiment in FIG. 1, it is provided that the separation stage 12 has a further cooling stage 21 downstream from the cooling stage 15 in terms of the process. This means that the gas mixture 6 is initially led through the cooling stage 15 and subsequently through the further cooling stage 21. It is further preferred that the cooling stage 15 and the further cooling stage 21 cool the gas mixture 6 to lower than 45° C. Thus, after passage through the two cooling stages 15, 21, the temperature of the gas mixture 6 is less than 45° C. In the present exemplary embodiment in FIG. 2, the gas mixture 6 is cooled to 40° C., at which temperature the gas mixture 6 enters into the deposition stage 14.

It is preferred that after separation of the crude methanol stream 13, the remaining gas mixture 6 is separated into the primary recycle stream 16 and the purge stream 17.

With regard to the further processing after the deposition stage 14, it is preferred that the purge stream 17 is fed from the deposition stage 14 to the scrubbing stage 18, in the present case the gas scrubber 18a, at essentially constant temperature, which in the present example is a temperature of 40° C. Alternatively or additionally, as likewise illustrated it may be provided that the primary recycle stream 16 from the deposition stage 14 is fed to the recycle compressor 19 at essentially constant temperature.

However, instead of achieving the lowest possible temperature for the deposition stage 14, a major portion of the methanol separation may be transferred into the above-mentioned scrubbing stage 18. For this purpose, a further preferred embodiment, which is implemented in the second exemplary embodiment in FIG. 2, provides that the crude methanol stream 13 is fed to a crude methanol cooling stage 22 for cooling the crude methanol stream 13, preferably with cooling to below 45° C. In the exemplary embodiment in FIG. 2, cooling to 40° C. takes place. In addition, prior to being fed to the scrubbing stage 18 the purge stream 17 may be fed to a purge stream cooling stage 23 for cooling the purge stream 15, wherein cooling to below 45° C. likewise preferably takes place. According to the exemplary embodiment in FIG. 2, cooling in particular to 40° C. takes place. Without the further cooling stage 21 in the first exemplary embodiment in FIG. 1, only the air cooler 15a cools prior to the deposition stage 14 in the second exemplary embodiment in FIG. 2, so that the temperature in the deposition stage 14 is 70° C. instead of 40° C.

As a result, the second exemplary embodiment in FIG. 2 provides two cooling stages, namely, the crude methanol cooling stage 22 and the purge stream cooling stage 23, each in different branches, downstream from the deposition stage 14 instead of one further cooling stage 21 upstream from the deposition stage 14. In the second exemplary embodiment, due to the described higher temperature in the deposition stage 14 this results in only 136,644 kg/h methanol in the crude methanol stream 13. When the purge stream 17, having a volume flow rate of 224,100 Nm$^3$/h, is led through the purge stream cooling stage 23 to the scrubbing stage 18, likewise at 40° C., and 2000 kg/h water at 40° C. is provided, crude methanol containing 4846 kg/h of methanol is thus scrubbed out. This methanol in turn passes from the sump of the gas scrubber 18a into the crude methanol stream 13 from the deposition stage 14, in particular downstream from the above-mentioned crude methanol cooling stage 22 in terms of the process, as illustrated in FIG. 2.

The gas scrubber 18a in the second exemplary embodiment in FIG. 2 differs from the gas scrubber 18a in FIG. 1 in that the packing inside the column ends at a farther distance from the base of the column due, among other things, to the fact that a higher level of the sump is expected on account of the anticipated larger quantity of scrubbed-out methanol. In addition, the gas scrubber 18a in the second exemplary embodiment has a separator unit between this packing and the base of the column. Another effect of the differences in the cooling is that the recycle compressor 19 in the first exemplary embodiment in FIG. 1 may be operated at lower power compared to the second exemplary embodiment in FIG. 2.

Another difference between the exemplary embodiments in FIG. 1 and FIG. 2 is the volume flow of the hydrogen-containing stream 3 from the pressure swing adsorption device 4. In the first exemplary embodiment (FIG. 1), the standard volume flow rate of the hydrogen-containing stream 3 corresponds to 148,140 Nm$^3$/h, and in the second exemplary embodiment (FIG. 2) corresponds to 142,570 Nm$^3$/h.

The reaction for the methanol synthesis is dependent on pressure, and is promoted by higher pressure. Accordingly, according to one preferred embodiment and as illustrated, the synthesis gas stream 2 is led through a synthesis gas compressor 24 for compression. In the present exemplary embodiments, synthesis gas, which is fed at 40° C. and a pressure of 56.3 bar, is brought to a pressure of 75 bar by the synthesis gas compressor 24. Since the above-mentioned recycle compressor 19 needs to compress only a smaller quantity than the synthesis gas compressor 24, the former may be operated at a higher pressure. On the one hand this is advantageous for the synthesis reaction in the secondary reactor stage 8, and on the other hand may also eliminate the need for recompressing the gas remaining after the further separation stage 25, described below. For this purpose, it is preferred that the final pressure of the recycle compressor 19 is higher than the final pressure of the synthesis gas compressor 24, and in particular that the final pressure of the recycle compressor 19 is at least 10% higher than the final pressure of the synthesis gas compressor 24.

It is provided in particular here that the synthesis gas stream 2, prior to being fed to the primary reactor stage 5, is fed to the secondary reactor stage 8 for gas cooling. Thus, when the secondary reactor stage 8 is a gas-cooled reactor as in the present exemplary embodiments, according to this variant the synthesis gas stream 2 provides the gas for cooling the secondary reactor stage 8. As illustrated in the figures, the hydrogen-containing stream 3 is preferably fed to the synthesis gas stream 2 upstream from the synthesis gas compressor 24 in terms of the process. The hydrogen-containing stream 3 generally does not have sufficient pressure when it exits from the hydrogen recovery stage 4.

In principle, it may be sufficient to provide only a single separation stage for separating methanol, even with an arrangement having two or more reactors. According to the illustrated exemplary embodiments, however, it is preferred that the methanol-containing product stream 9 is fed to a further separation stage 25 for separating a further crude methanol stream 26 composed essentially of water and methanol. In the first exemplary embodiment in FIG. 1, the further crude methanol stream 26 contains 74,689 kg/h methanol in the crude methanol. Thus, 227,551 kg/h methanol is recovered overall, i.e., via this further crude methanol stream 26 and via the crude methanol from deposition stage 14 and the scrubbing stage 18.

Due, among other things, to the overall lower degree of separation of crude methanol via the separation stage 12 and the scrubbing stage 18 in the second exemplary embodiment, the further crude methanol stream 26 in the second exemplary embodiment in FIG. 2 contains 88,319 kg/h methanol in the crude methanol. Consequently, a total of 229,859 kg/h methanol is obtained in the second exemplary embodiment.

Residual gas remains even after this separation of the further crude methanol stream 26. Accordingly, it is preferred that a secondary recycle stream 27, which in this case is made up of the residual gas of the methanol-containing product stream 9 or essentially of the residual gas, that remains after separation of the further crude methanol stream 26 is fed to the synthesis gas stream 2. Since, as described above, in the present exemplary embodiments the recycle compressor 19 is operated at a final pressure that exceeds the final pressure of the synthesis gas compressor 24, according to one preferred embodiment illustrated here the secondary recycle stream 27 may be fed to the synthesis gas stream 2 downstream from the synthesis gas compressor 24 in terms of the process. Thus, since the synthesis gas compressor 24 itself does not have to process the corresponding volume, load on the synthesis gas compressor 24 is relieved. In the present exemplary embodiments the secondary recycle stream 27 exits from the further separation stage 25 at a pressure of 75.9 bar, which is sufficiently close to the final pressure of the synthesis gas compressor 24 of 75 bar. In the exemplary embodiment in FIG. 1, the secondary recycle stream 27 has a volume flow rate of 468,892 Nm$^3$/h, and in the exemplary embodiment in FIG. 2 has a volume flow rate of 456,652 Nm$^3$/h.

One preferred embodiment further provides that the secondary recycle stream 27 has a molar fraction of carbon dioxide that is at least twice the molar fraction of carbon monoxide in the secondary recycle stream 27. This means that the carbon monoxide in the secondary reactor stage 8 has been largely converted into methanol, which in turn allows increased conversion of the carbon dioxide into methanol. The carbon dioxide may be effectively used for the methanol synthesis in this way.

Analogously to the separation stage 12 downstream from the primary reactor stage 5, the further separation stage 25 may include a secondary cooling stage 28 and a secondary deposition stage 29, in the present exemplary embodiments the methanol-containing product stream 9 being cooled to 40° C. and exiting from the secondary cooling stage 28 at a pressure of 76 bar.

Similarly, the secondary recycle stream 27 also has essentially this low temperature, which may advantageously be used for precooling the methanol-containing product stream 9, which in this case exits from the secondary reactor stage 8 at 220° C. Therefore, it is preferred that the secondary recycle stream 27, in particular prior to being fed to the synthesis gas stream 2, is led through a trimmable heat exchanger assembly 30 for cooling the methanol-containing product stream 9, in that the methanol-containing product stream 9 is also led through the heat exchanger assembly 30. The cooling of the methanol-containing product stream 9 thus takes place due to a temperature exchange occurring between the methanol-containing product stream 9 and the secondary recycle stream 27 in the heat exchanger assembly 30. The trimmability of the heat exchanger assembly 30 may in principle be achieved in any desired manner, and as in the exemplary embodiments, by leading an in particular variable portion of the methanol-containing product stream 9 together with the secondary recycle stream 27 around the temperature exchange.

According to one preferred embodiment, the primary reactor stage 5 is an isothermal water-cooled reactor.

Accordingly, feed water 31 may be fed to the primary reactor stage 5 for water cooling. The comparatively low outlet temperature of the feed water may also be used for precooling the methanol-containing product stream 9, in particular by leading the feed water 31 through a water heat exchanger 32, through which the methanol-containing product stream 9 is also led for heat exchange, before feeding the feed water to the primary reactor stage 5. Temperature exchange between the feed water 31 and the methanol-containing product stream 9 thus takes place in the water heat exchanger 32 for the purpose of cooling.

As stated above, the synthesis gas stream 2 is preferably obtained from the above-mentioned carbon-containing energy carrier stream 1. This carbon-containing energy carrier stream 1 may in principle be of any type. The proposed method has proven to be particularly suitable when, as preferred, the carbon-containing energy carrier stream 1 includes a natural gas stream 1a or is composed essentially of this natural gas stream 1a. Consequently, the energy carrier stream 1 may contain methane, ethane, propane, and in some cases also butane. The natural gas stream may also be supplied from a plurality of geographically distributed natural gas deposits. This may result in a particularly nonuniform distribution of the above-mentioned components of the natural gas, which in turn affects the relative molar fractions of hydrogen, carbon monoxide, and carbon dioxide. The proposed method allows preparation to be made for a more or less strongly pronounced deficiency of hydrogen by adjusting the distribution between the first portion 7 and the second portion 10 of the residual gas.

Figure 3:
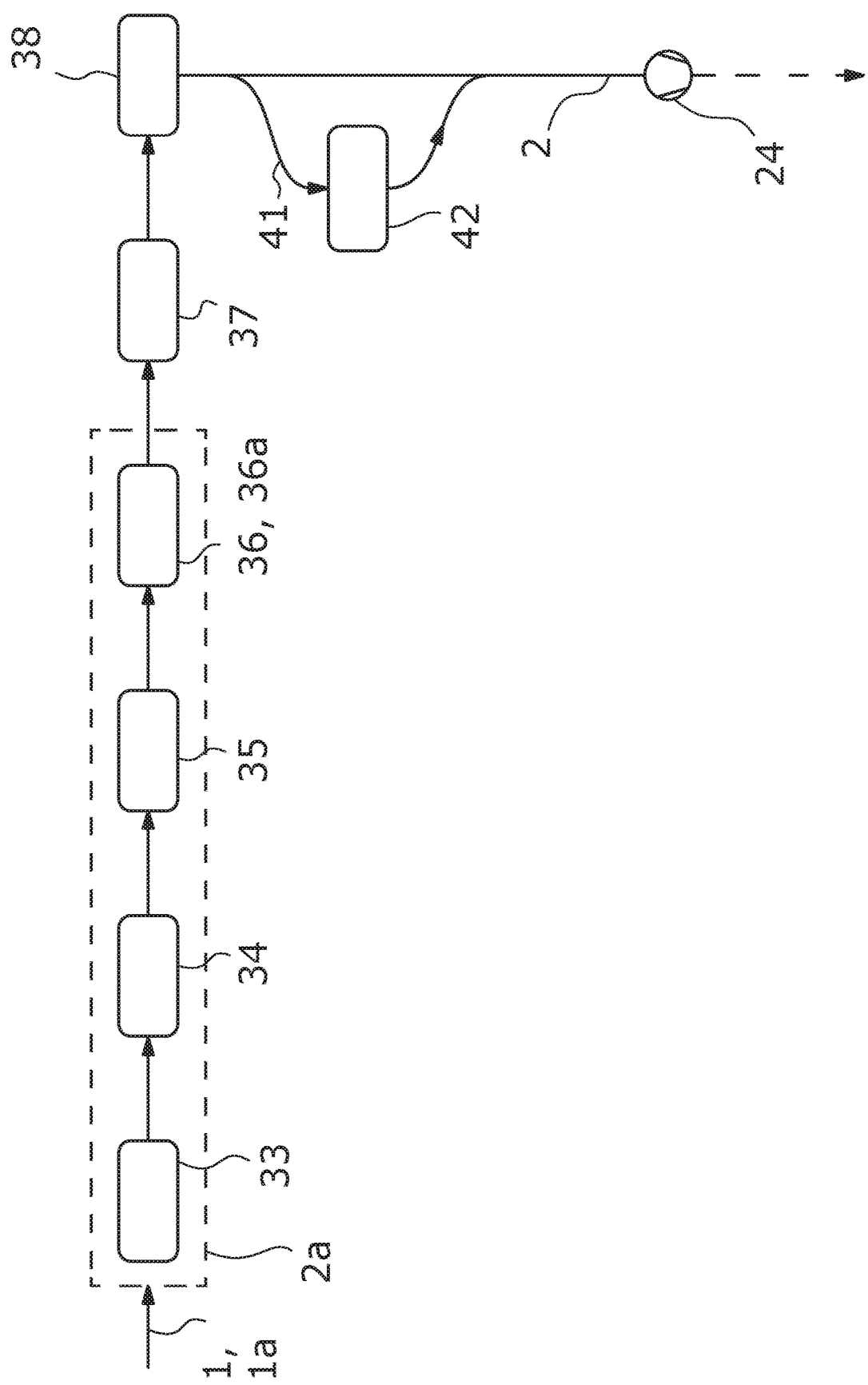
FIG. 3 shows the flow diagram of a first variant of a feed unit for a system for carrying out the proposed method.
Figure 4:
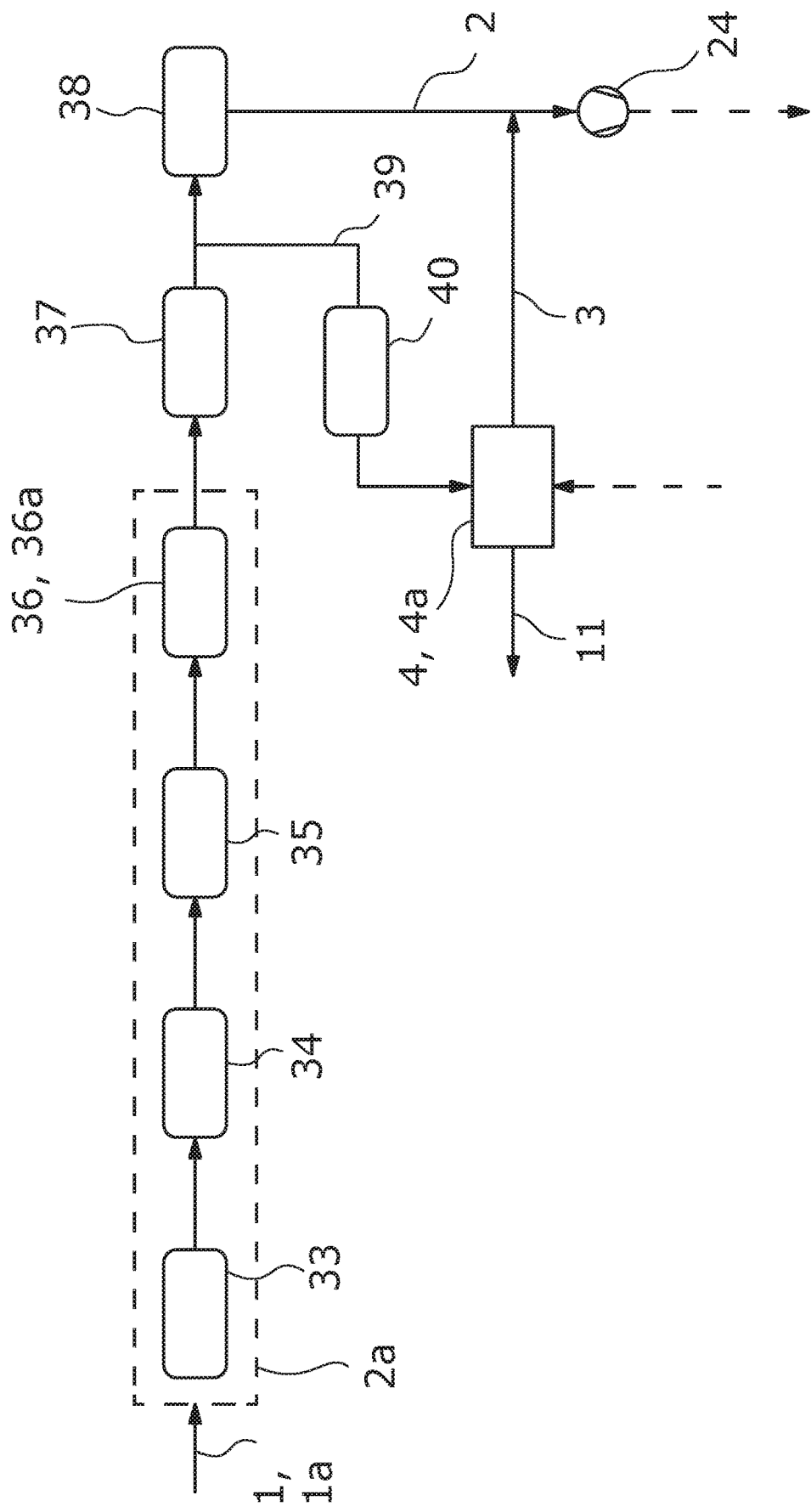
FIG. 4 shows the flow diagram of a second variant of a feed unit for a system for carrying out the proposed method.

A first and a second preferred exemplary embodiment of a feed unit 2b for providing a synthesis gas stream 2 are illustrated in FIG. 3 and FIG. 4, respectively. Both variants of the feed unit 2b are basically combinable in any desired manner with the respective exemplary embodiments in FIGS. 1 and FIG. 2. Unless stated otherwise, the following discussion concerning the feed unit 2b in principle refers to the variant in FIG. 3 and to the variant in FIG. 4.

The synthesis gas stream 2 is preferably obtained from the natural gas stream 1a in a manner known per se by feeding the natural gas stream 1a to a desulfurization device 33 for the purpose of desulfurization, and subsequently to a saturator 34 for saturation with water vapor. The natural gas stream that is desulfurized and saturated in this way is fed to an adiabatic prereformer 35 in which higher hydrocarbons in the natural gas stream 1a are converted into a mixture containing methane, hydrogen, and carbon oxides by steam reforming. This mixture is then converted in an autothermal reformer 36, in a manner known per se, into synthesis gas composed essentially of hydrogen, carbon monoxide, and carbon dioxide. It is therefore preferred that the synthesis gas stream 2 is obtained from the energy carrier stream 1 in an autothermal reforming stage 36a, which in the present case is formed by the autothermal reformer 36; in the autothermal reforming stage 36a, a catalytic, partial oxidation provides the heat required for the endothermal steam reforming reactions. It is preferred that the synthesis gas stream 2 obtained in the autothermal reforming stage 36a has a molar ratio once again given by $$S = \frac{n(\mathrm{H_2}) - n(\mathrm{CO_2})}{n(\mathrm{CO}) + n(\mathrm{CO_2})},$$

where n is expressed in moles, of S<2 and in particular S<1.8.

Obtaining the synthesis gas stream 2 from the energy carrier stream 1, and in particular the catalytic partial oxidation, preferably take place in the autothermal reforming stage 36a with feeding of an oxygen-enriched stream. Correspondingly, an oxygen stream line for feeding the oxygen-enriched stream to the autothermal reforming stage 36a is preferably provided, wherein this oxygen stream line may in particular be encompassed by the proposed system. As a result of using an oxygen-enriched stream, in contrast to using an air stream, which thus contains a standard proportion of oxygen, the proportion of nitrogen in the synthesis gas stream is greatly reduced. Much lower volumes of gas thus need to be processed in the system, which, in particular for the compressors, allows much smaller dimensioning and lower power consumption, and therefore offers significant cost savings.

The oxygen-enriched stream has an increased proportion of oxygen compared to ambient air. Thus, the oxygen-enriched stream has a molar oxygen proportion of at least 40%. The oxygen-enriched stream is preferably composed predominantly of oxygen. Accordingly, the oxygen-enriched stream has a molar oxygen proportion of at least 50%, preferably at least 80%, and in particular at least 90%. It is also possible for the oxygen-enriched stream to be composed essentially of oxygen.

Furthermore, it is preferred that the oxygen-enriched stream is obtained from an air separation (ASU). This air separation unit is a device for separating air into multiple material streams, in which the main components, nitrogen and oxygen, are present with respectively different levels of enrichment. For example, this air separation unit may carry out the separation according to the Linde process. This air separation unit is preferably encompassed by the proposed system. In that case, the oxygen stream line leads from the air separation unit to the autothermal reforming stage 36a.

Following the autothermal reforming stage 36a, the synthesis gas stream 2 thus obtained is cooled in a waste heat waste heat unit 37. A further cooling unit 38 for cooling the synthesis gas stream 2 may be provided downstream from the waste heat unit in terms of the process. FIGS. 1 and 2 illustrate the synthesis gas compressor 24 from FIGS. 3 and 4 as the subsequent process stage. The totality of the units for obtaining the synthesis gas stream 2 from the energy carrier stream 1 may also be referred to as a synthesis gas source 2a. In the present exemplary embodiments, the synthesis gas source includes the desulfurization device 33, the saturator 34, the prereformer 35, and the autothermal reformer 36.

Frequently, in the production of the synthesis gas for the synthesis gas stream 2, and in particular in the above-mentioned autothermal reforming, the optimal stoichiometry number for the methanol synthesis is not achieved in the synthesis gas. It may therefore be advantageous, particularly in the extreme case when higher hydrocarbons are present, to provide, prior to the methanol synthesis, further measures for appropriately adjusting the stoichiometry number. In particular when the synthesis gas from the production has a stoichiometry number, which is determined here from the formula $$S = \frac{n(\mathrm{H_2}) - n(\mathrm{CO_2})}{n(\mathrm{CO}) + n(\mathrm{CO_2})},$$

of less than 2, where n is expressed in moles, increasing the stoichiometry number of the synthesis gas stream to greater than 2 is advantageous.

In this regard, a first preferred variant, shown in the variant in FIG. 4, provides that a shift substream 39 is branched off from the synthesis gas stream 2 prior to feeding the hydrogen-containing stream 3 and is fed to a shift device 40 in which the shift substream 39 is at least partially converted into carbon dioxide and hydrogen via a water-gas shift reaction, and that the carbon dioxide and the hydrogen from the shift device 40 are fed to the hydrogen recovery stage 4. The shift device 40 and the hydrogen recovery stage 4, as already illustrated in FIGS. 1 and 2 and described above, are shown in FIG. 4. The carbon dioxide together with the waste gas 11 is then removed, whereas the hydrogen thus obtained is fed, via the hydrogen-containing stream 3, to the synthesis gas stream 2 and is thus available for the methanol synthesis. This removal of the carbon dioxide and retention of the hydrogen results in an increase in the stoichiometry number.

Alternatively or additionally, the variant illustrated in FIG. 3 may be provided, according to which a scrubber substream 41 is removed from the synthesis gas stream 2, and the scrubber substream is fed to a scrubber device 42 for scrubbing carbon dioxide from the scrubber substream 41. The scrubbing of carbon dioxide may in principle take place in any desired manner. This measure also increases the stoichiometry number.

The feed unit 2b may include the synthesis gas source 2a as well as the other devices described with reference to FIGS. 3 and 4.

The proposed system, an exemplary embodiment of which is correspondingly illustrated in each of FIGS. 1 and 2, for the synthesis of methanol includes a feed unit 2b for providing a synthesis gas stream 2 with hydrogen and carbon oxides. The proposed system also includes a hydrogen recovery stage 4 from which a hydrogen-containing stream 3 is fed to the synthesis gas stream 2, and also includes a primary reactor stage 5 to which the synthesis gas stream 2 is fed, and in which the synthesis gas stream 2 is catalytically, partially converted into a gas mixture 6 containing water, methanol, and residual gas, wherein a first portion 7 of the residual gas is fed to the hydrogen recovery stage 4 for separation into the hydrogen-containing stream 3 and a waste gas stream 11.

The proposed system is characterized in that it has a secondary reactor stage 8 to which a second portion 10 of the residual gas is fed for further catalytic, at least partial, conversion into a methanol-containing product stream 9.

Further special, preferred embodiments and features of the proposed system result from the corresponding embodiments and features of the proposed method.

The invention claimed is:

1. A method for the synthesis of methanol, including the following steps: feeding a hydrogen-containing stream from a hydrogen recovery stage into a synthesis gas stream containing hydrogen and carbon oxides, and feeding the synthesis gas stream to a primary reactor stage for the catalytic and partial conversion of the synthesis gas stream into a gas mixture containing water, methanol, and residual gas, and feeding a first portion of the residual gas to the hydrogen recovery stage for separation into the hydrogen-containing stream and a waste gas stream, wherein a second portion of the residual gas is fed to a secondary reactor stage for further catalytic and at least partial conversion into a methanol-containing product stream, wherein the gas mixture is fed to a separation stage for separating a crude methanol stream, wherein the methanol-containing product stream is fed to another separation stage for separating a further crude methanol stream, and wherein a secondary recycling stream remaining after the separation of the further crude methanol stream is fed into the synthesis gas stream.

2. The method according to claim 1, wherein the synthesis gas stream, prior to feeding of the hydrogen-containing stream, has a molar ratio, given by $$S = \frac{n(H_2) - n(CO_2)}{n(CO) + n(CO_2)},$$

of S<2, and that a molar ratio of S>2 is present in the primary reactor stage.

3. The method according to claim 1, wherein in the secondary reactor stage, a molar ratio S, given by $$S = \frac{n(H_2) - n(CO_2)}{n(CO) + n(CO_2)},$$

is present which is greater, than the molar ratio S that is present in the primary reactor stage.

4. The method according to claim 1, wherein the first portion of the residual gas and the second portion of the residual gas are separated by means of a stream division of the gas mixture into at least one primary recycling stream, comprising the second portion, for being fed to the secondary reactor stage, and a purge stream, comprising the first portion, for being fed to the hydrogen recovery stage.

5. The method according to claim 4, wherein the purge stream, prior to being fed to the hydrogen recovery stage, is fed to a scrubbing stage for scrubbing out methanol remaining in the purge stream.

6. The method according to claim 4, wherein the primary recycling stream is led through a recycling compressor for compression, and/or that the primary recycling stream is led through a primary recycling heat exchanger for cooling the gas mixture.

7. The method according to claim 1, wherein the separation stage has a deposition stage which separates the crude methanol stream as a condensate of the gas mixture.

8. The method according to claim 7, wherein the gas mixture is cooled before being divided into the first portion and the second portion of the residual gas.

9. The method according to claim 1, wherein the synthesis gas stream is led through a synthesis gas compressor for compression.

10. The method according to claim 1, wherein the secondary recycling stream is fed into the synthesis gas stream downstream from the synthesis gas compressor in terms of the process.

11. The method according to claim 1, wherein the secondary recycling stream has a molar proportion of carbon dioxide which is at least twice the molar proportion of carbon monoxide in the secondary recycling stream.

12. The method according to claim 1, wherein the synthesis gas stream is obtained from a carbonaceous energy carrier stream.

13. The method according to claim 12, wherein the synthesis gas stream is obtained from the energy carrier stream in an autothermal reformation stage, wherein in the autothermal reformation stage (36a) a catalytic partial oxidation provides the heat required for the endothermic steam reformation reactions.

14. The method according to claim 1, wherein a scrubber sub stream is removed from the synthesis gas stream, and the scrubber sub stream is fed to a scrubber device for scrubbing carbon dioxide from the scrubber substream.

15. A system for the synthesis of methanol, comprising a feeding assembly for providing a synthesis gas stream with hydrogen and carbon oxides, comprising a hydrogen recovery stage from which a hydrogen-containing stream is fed into the synthesis gas stream, and comprising a primary reactor stage to which the synthesis gas stream is fed and in which the synthesis gas stream is catalytically and partially converted into a gas mixture with water, methanol, and residual gas, wherein a first portion of the residual gas is fed to the hydrogen recovery stage for separation into the hydrogen-containing stream and a waste gas stream, wherein the system has a secondary reactor stage to which a second portion of the residual gas is fed for further catalytic and at least partial conversion into a methanol-containing product stream, wherein the gas mixture is fed to a separation stage for separating a crude methanol stream, wherein the methanol-containing product stream is fed to another separation stage for separating a further crude methanol stream, and wherein a secondary recycling stream remaining after the separation of the further crude methanol stream is fed into the synthesis gas stream.

* * * * *